United States Patent [19]
Gough et al.

[11] Patent Number: 5,800,484
[45] Date of Patent: Sep. 1, 1998

[54] MULTIPLE ANTENNA ABLATION APPARATUS WITH EXPANDED ELECTRODES

[75] Inventors: Edward J. Gough, Menlo Park; Alan A. Stein, Moss Beach; Stuart D. Edwards, Portola Valley; Patrick J. Burns, Kentfield, all of Calif.

[73] Assignee: Rita Medical Systems, Inc., Mountain View, Calif.

[21] Appl. No.: 707,250

[22] Filed: Sep. 3, 1996

Related U.S. Application Data

[63] Continuation-in-part of Ser. No. 605,323, Feb. 14, 1996, which is a continuation-in-part of Ser. No. 515,379, Aug. 15, 1995, Pat. No. 5,683,384.

[51] Int. Cl.⁶ ............................................. A61B 17/39
[52] U.S. Cl. ........................... 607/104; 607/101; 606/41
[58] Field of Search .................... 606/41, 42, 45–52; 607/100–102, 104, 105; 604/21, 22

[56] References Cited

U.S. PATENT DOCUMENTS

| | | | |
|---|---|---|---|
| 5,401,272 | 3/1995 | Perkins | 606/15 |
| 5,403,311 | 4/1995 | Abele et al. | 606/49 |
| 5,437,662 | 8/1995 | Nardella | 606/40 |
| 5,472,441 | 12/1995 | Edwards et al. | 606/41 |
| 5,505,730 | 4/1996 | Edwards | 606/41 |
| 5,507,743 | 4/1996 | Edwards et al. | 606/41 |

FOREIGN PATENT DOCUMENTS 2124684  11/1972  Germany.

*Primary Examiner*—Michael Peffley
*Attorney, Agent, or Firm*—Wilson Sonsini Goodrich & Rosati

[57] ABSTRACT

An ablation apparatus has an introducer including an introducer lumen, a proximal portion and a distal portion. A handpiece with a proximal portion and a distal portion is coupled to the introducer proximal portion. Two or more electrodes are at least partially positioned in the introducer lumen. Each electrode is configured to be advanced from the introducer distal portion in a deployed state into a selected tissue site to define a volumetric ablation volume. A fluid delivery member is positioned on at least a portion of an exterior of one of the electrodes. The fluid delivery member is configured to be coupled to a fluid medium source. A cable is coupled to the electrodes.

12 Claims, 10 Drawing Sheets

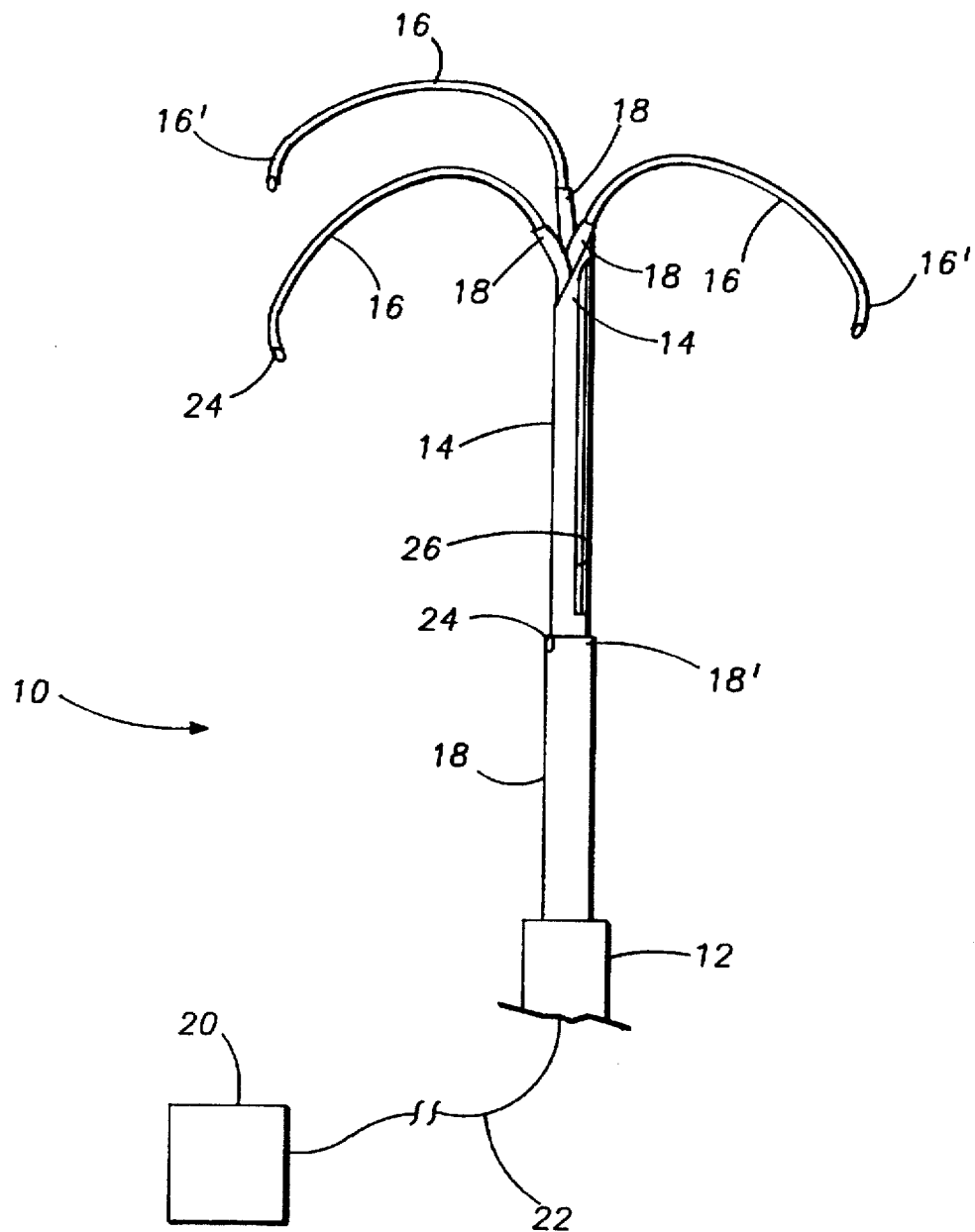
FIG.—1A

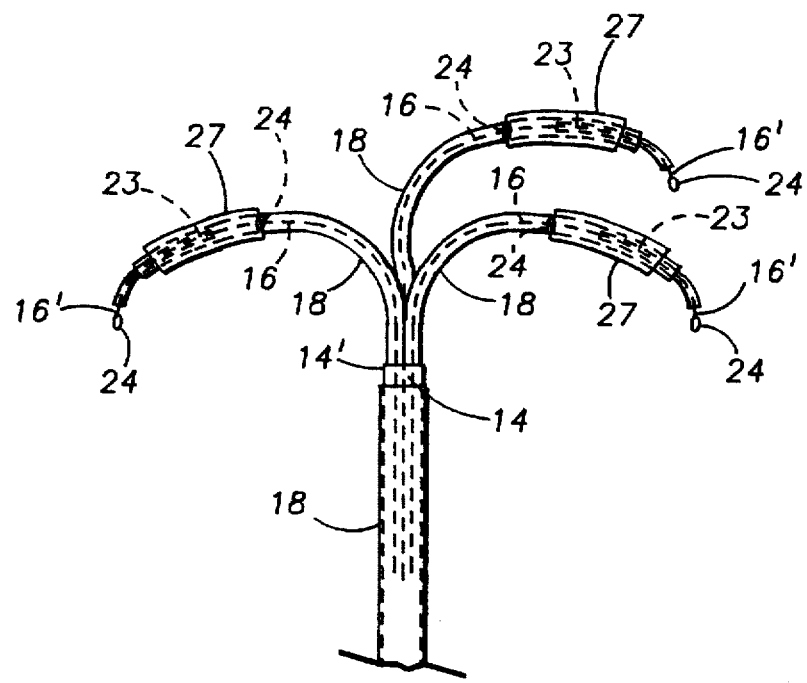
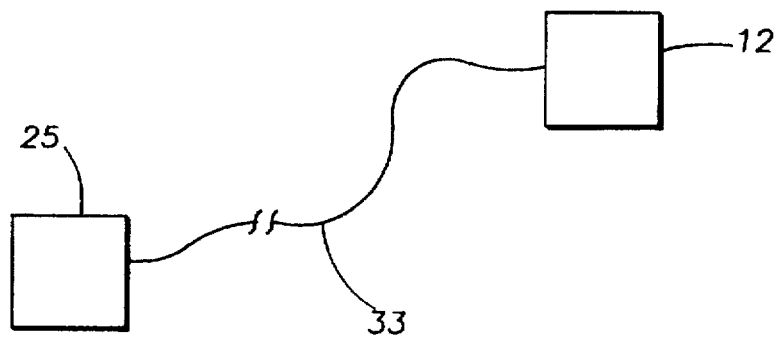
FIG.—1B

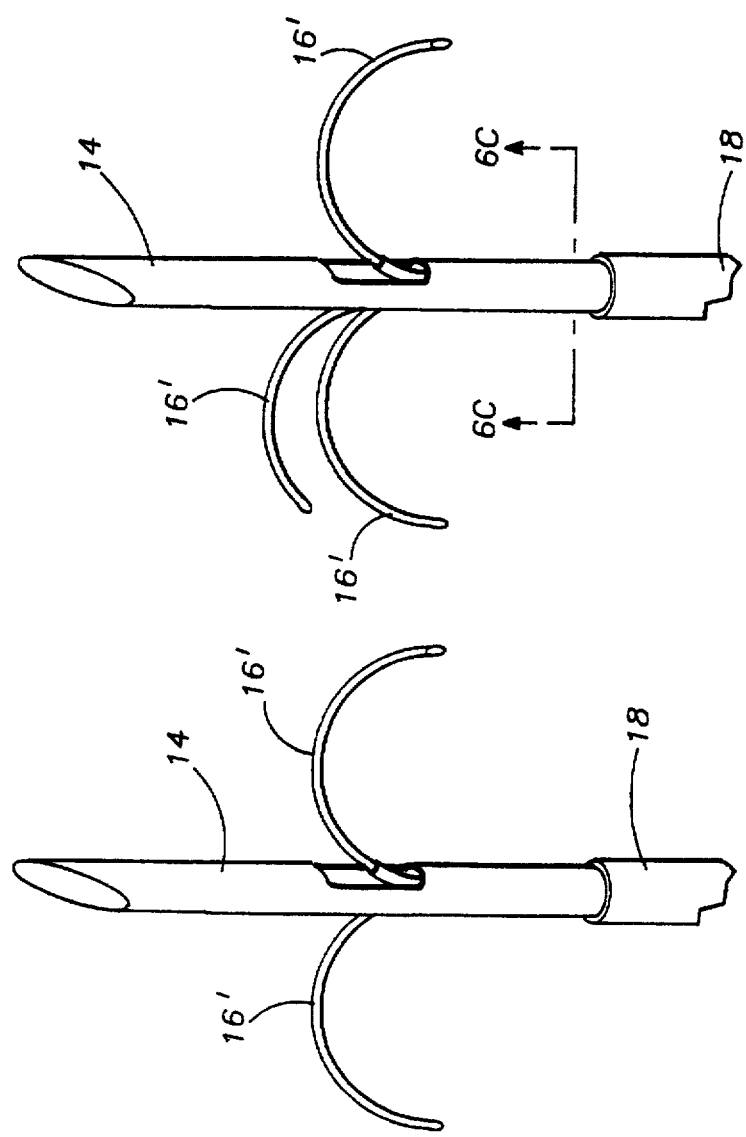

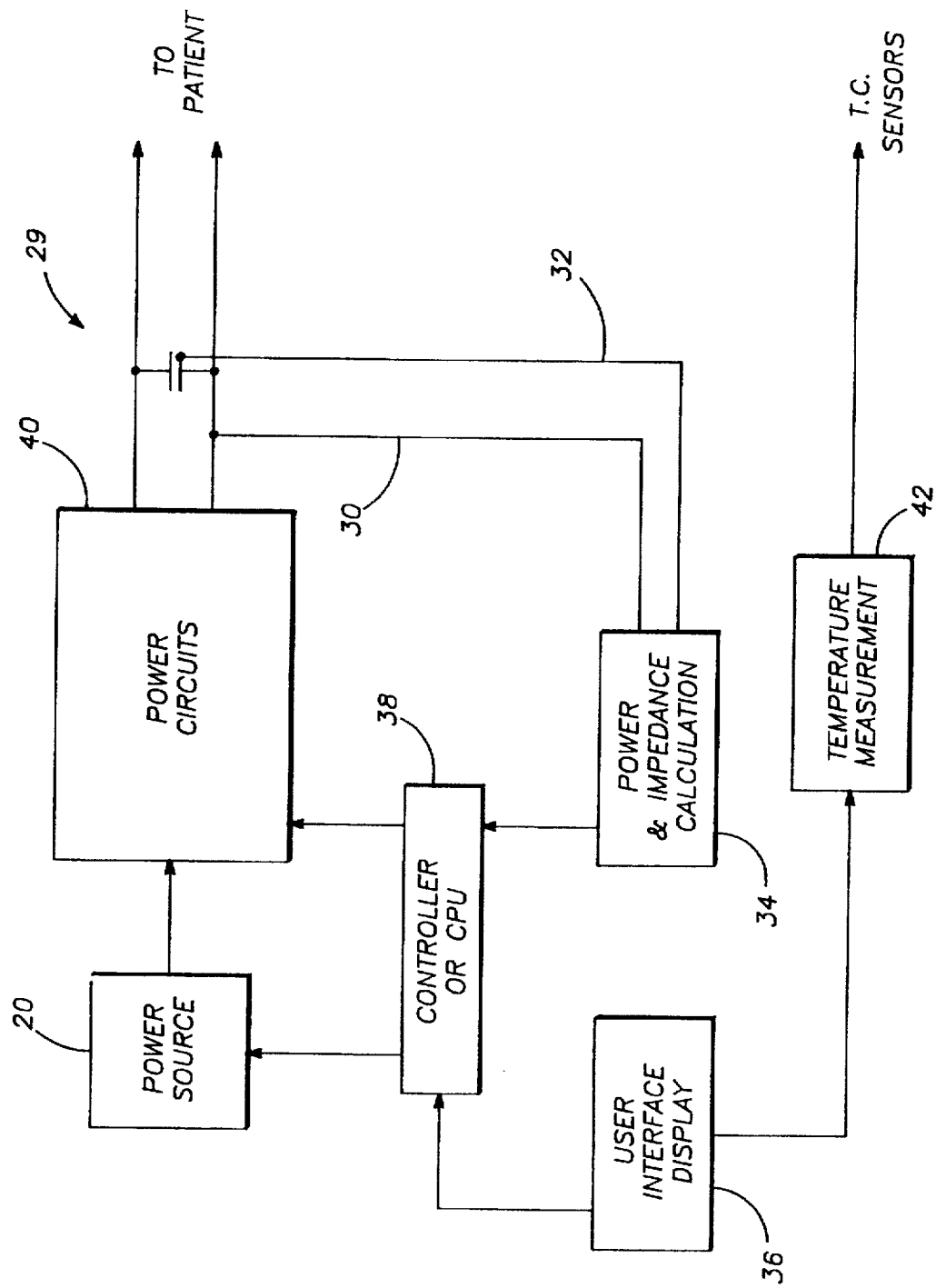

MULTIPLE ANTENNA ABLATION APPARATUS WITH EXPANDED ELECTRODES

REFERENCE TO RELATED APPLICATION

This application is a continuation-in-part of U.S. patent application Ser. No. 08/605,323, filed Feb. 14, 1996, entitled "Multiple Antenna Ablation Apparatus", which is a continuation-in-part of 08/515,379, filed Aug. 15, 1995 now U.S. Pat. No. 5,683,384, entitled "Multiple Antenna Ablation Apparatus", both incorporated herein by reference.

BACKGROUND OF THE INVENTION

1. Field of the Invention

This invention relates generally to a multiple antenna ablation apparatus, and more particularly to a multiple antenna ablation apparatus with two or more electrodes advanceable from an introducer to surround a selected tissue mass and at least one of the electrodes includes a microporous membrane positioned at an exterior of the electrode.

2. Description of the Related Art

Current open procedures for treatment of tumors are extremely disruptive and cause a great deal of damage to healthy tissue. During the surgical procedure, the physician must exercise care in not cutting the tumor in a manner that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed, (i) changes in cell or nuclear membrane permeability or fluidity, (ii) cytoplasmic lysosomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the skin.

Attempts to use interstitial local hyperthermia have not proven to be very successful. Results have often produced nonuniform temperatures throughout the tumor. It is believed that tumor mass reduction by hyperthermia is related to thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

There is a need for an ablation apparatus which introduces two or more electrodes in a surrounding relationship to a selected ablation mass, defining an ablation volume, coupled with a member to deliver an electrolytic solution to the selected ablation mass. There is a further need for an ablation apparatus which introduces an electrode into a selected ablation mass, applies a compression force to the selected ablation mass, and delivers an electrolytic solution to the selected ablation mass.

SUMMARY OF THE INVENTION

Accordingly, an object of the invention is to provide an ablation device which is introduced into a selected tissue mass.

Another object of the invention is to provide an ablation apparatus which introduces two or more electrodes in a surrounding relationship to a selected ablation mass and also delivers an electrolytic solution to the selected ablation mass.

Yet another object of the invention is to provide an ablation apparatus which introduces an electrode into a selected ablation mass, applies a compression force to the selected ablation mass, and delivers an electrolytic solution to the selected ablation mass.

These and other objects of the invention are achieved in an ablation apparatus with an introducer including an introducer lumen, a proximal portion and a distal portion. A handpiece with a proximal portion and a distal portion is coupled to the introducer proximal portion. Two or more electrodes are at least partially positioned in the introducer lumen. Each electrode is configured to be advanced from the introducer distal portion in a deployed state into a selected tissue site to define a volumetric ablation volume. A fluid delivery member is positioned on at least a portion of an exterior of one of the electrodes. The fluid delivery member is configured to be coupled to a fluid medium source. A cable is coupled to the electrodes.

In another embodiment, the ablation apparatus includes an expandable member positioned at an exterior surface of the introducer. The expandable member is configured to be coupled to a source of an expansion medium. A fluid delivery member is at least partially positioned at an exterior surface of the expandable member. The fluid delivery member is configured to be coupled to an electrolytic solution source. An electrode is coupled to the fluid delivery member and a cable is coupled to the electrode.

BRIEF DESCRIPTION OF THE FIGURES

FIG. 1(a) is a perspective view of the multiple antenna ablation apparatus of the present invention illustrating a trocar and three laterally deployed antennas.

FIG. 1(b) is a perspective view of the multiple antenna ablation apparatus of the present invention including one or more fluid delivery members in a surrounding relationship to an exterior of a deployed electrode.

FIG. 6(a) is a perspective view of the multiple antenna ablation of the present invention illustrating two antennas which provide a retaining and gripping function.

FIG. 6(b) is a perspective view of the multiple antenna ablation of the present invention illustrating three secondary antennas which provide a retaining and gripping function.

FIG. 6(c) is a cross-sectional view of the apparatus of FIG. 6(b) taken along the lines 6(c)—6(c).

FIG. 9 is a block diagram illustrating the inclusion of a controller, electromagnetic energy source and other electronic components of the present invention.

DETAILED DESCRIPTION

Figure 1C:
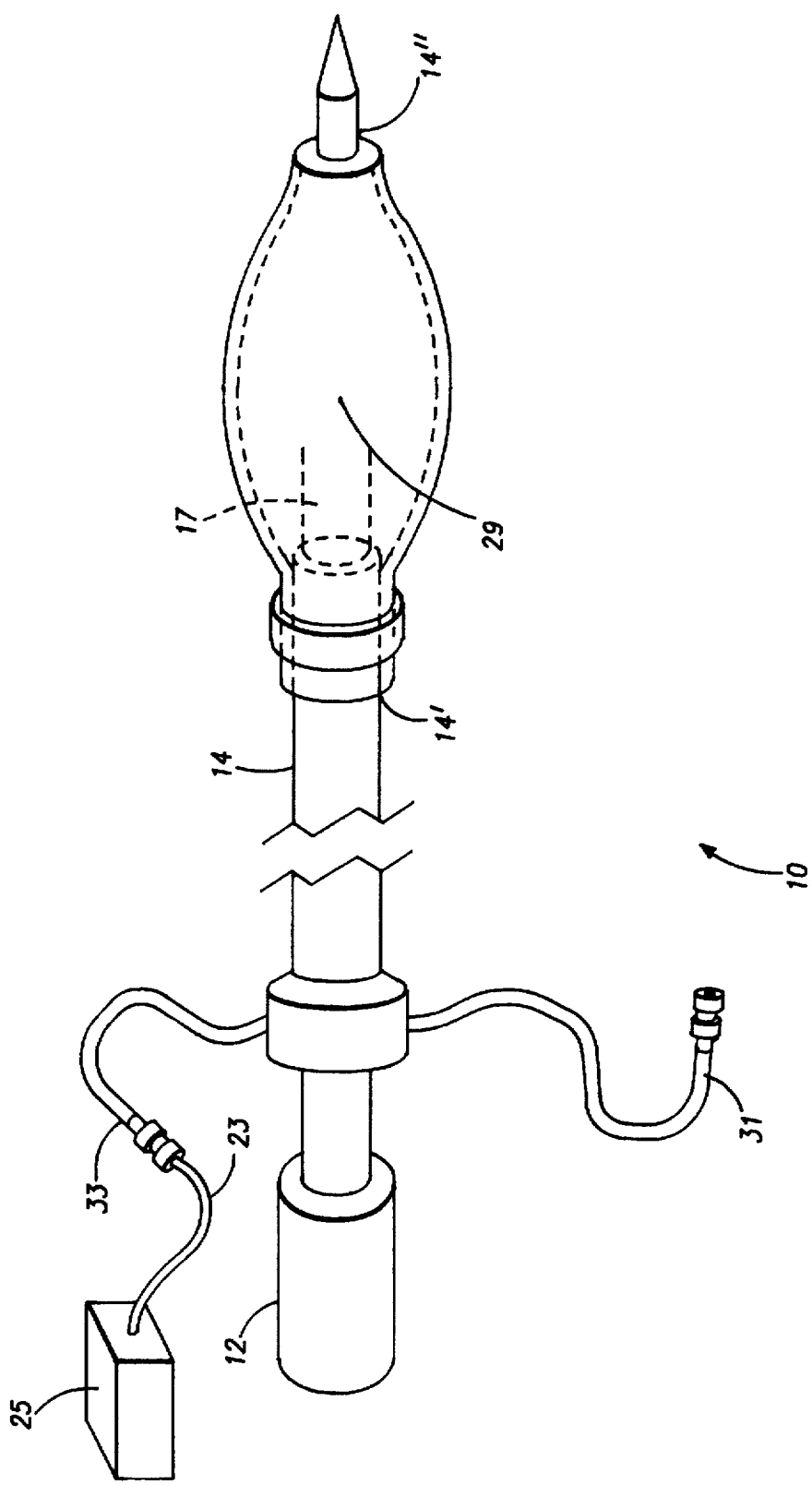
FIG. 1(c) is a perspective view of an ablation apparatus of the present invention that includes an introducer, an expandable member, a fluid delivery device and one or more electrodes.

As shown in FIG. 1(a), multiple antenna ablation device 10 includes a handpiece 12 includes a trocar 14, and one or more antennas 16, including RF, microwave shortwave, and the like (hereafter collectively referred to as "electrodes"). Electrodes 16 are initially positioned in a trocar lumen when trocar 14 is advanced through tissue. When trocar 14 reaches a selected tissue ablation site in a selected tissue mass, including but not limited to a solid lesion, electrodes 16 are laterally deployed relative to the trocar's longitudinal axis from the trocar lumen into the selected tissue mass. Volumetric ablation proceeds from the interior of the selected tissue mass in a direction towards a periphery of the selected tissue mass.

Each electrode has a distal portion 16' which extends in a lateral direction relative to a longitudinal axis of trocar 14. Unless distal portion 16' has insulation, then its entire length of extension is an electromagnetic energy delivery surface which delivers electromagnetic energy to the selected tissue mass. The length and size of each electromagnetic energy delivery surface can be variable. In one embodiment, each electrode 16 has an electromagnetic energy delivery surface length of 0.25 inches or less, and an outer diameter for electrode 16 of about 0.072 inches or less.

Lengths of electrodes 16 can be adjustable. Trocar 14 can be moved up and down, rotated about its longitudinal axis, and moved back and forth, in order to define, along with sensors, the periphery or boundary of the selected tissue mass, including but not limited to a tumor. This provides a variety of different geometries, not always symmetrical, that can be ablated. Volumetric ablation is defined as the creation of an ablation with a periphery formed in between adjacent distal portions 16'. The volume of non-ablated tissue between adjacent distal portions 16' is minimized. A variety of different geometric ablations are achieved including but not limited to spherical, semi-spherical, spheroid, triangular, semi-triangular, square, semi-square, rectangular, semi-rectangular, conical, semi-conical, quadrilateral, semi-quadrilateral, semi-quadrilateral, rhomboidal, semi-rhomboidal, trapezoidal, semi-trapezoidal, combinations of the preceding, geometries with non-planar sections or sides, free-form and the like.

In one embodiment, trocar 14 can have a sharpened distal portion 14' to assist introduction through tissue. Distal portion 16' is the section of electrode 16 that is advanced from trocar 14 and into the selected tissue mass. Each electrode 16 has a distal portion 16' that can be constructed to be less structurally rigid than trocar 14. Structural rigidity is determined by, (i) choosing different materials for trocar 14 and distal end 16' or some greater length of electrode 16, (ii) using the same material but having less of it for electrode 16 or distal portion 16', e.g., electrode 16 or distal portion 16' is not as thick as trocar 14, or (iii) including another material in trocar 14 or an electrode 16 to vary their structural rigidity. For purposes of this disclosure, structural rigidity is defined as the amount of deflection that an electrode has relative to its longitudinal axis. It will be appreciated that a given electrode will have different levels of rigidity depending on its length.

Electrodes 16 can be made of a variety of conductive materials, both metallic and non-metallic. One suitable material is type 304 stainless steel of hypodermic quality. In some applications, all or a portion of secondary electrode 16 can be made of a shaped memory metal, such as NiTi, commercially available from Raychem Corporation, Menlo Park, Calif.

Each of the electrodes 16 can have different lengths. The lengths can be determined by the actual physical length of an electrode 16, the length of an electrode electromagnetic energy delivery surface, and the length of an electrode 16 that is not covered by an insulator. Suitable lengths include but are not limited to 17.5 cm, 25.0 cm, and 30.0 cm. The actual length of an electrode 16 depends on the location of the selected tissue mass to be ablated, its distance from the skin, its accessibility as well as whether or not the physician chooses a laparoscopic, percutaneous or other procedure.

An insulation sleeve 18 may be positioned around an exterior of trocar 14 and/or electrodes 16. All or some of insulation sleeves 18 may be adjustably positioned so that the length of an electrode electromagnetic energy delivery surface can be varied. Each insulation sleeve 18 surrounding a trocar 14 can include one or more apertures. This permits the introduction of a electrode 16 through trocar 14 and insulation sleeve 18.

In one embodiment, insulation sleeve 18 comprises a polyamide material. A sensor 24 may be positioned on top of polyimide insulation sleeve 18. The polyamide insulation sleeve 18 is semi-rigid. Sensor 24 can lay down substantially along the entire length of polyamide insulation sleeve 18. Trocar 14 is made of a stainless-steel hypodermic tubing. Electrodes 16 have distal portions 16' that are made of a variety of different materials including but not limited to NiTi hypodermic tubing. A handpiece 12 is included with markings to show the length of lateral deployment of electrodes 16 from trocar 14. Fluid infusion is delivered through a Luer port at a side of the handpiece 12. Type-T thermocouples are positioned at distal portions 16'.

An electromagnetic energy source 20 is connected to multiple electrode device 10 with one or more cables 22. Electromagnetic energy source 20 can be an RF source, microwave source, short wave source, laser source and the like. Multiple electrode device 10 can be comprised of electrodes 16 that are RF electrodes, microwave electrodes, as well as combinations thereof Electromagnetic energy source 20 may be a combination RF/microwave box. Further a laser optical fiber, coupled to a laser source 20 can be introduced through one or both of trocar 14 or a electrode 16. Trocar 14 and/or a secondary electrode 16 can be an arm for the purposes of introducing the optical fiber.

Electrodes 16 are electromagnetically coupled to electromagnetic energy source 20. The coupling can be direct from electromagnetic energy source 20 to each electrode 16, or indirect by using a collet, sleeve and the like which couples one or more electrodes 16 to electromagnetic energy source 20. Electromagnetic energy can be delivered from one electrode 16 to another.

One or more sensors 24 may be positioned on at least a portion of interior or exterior surfaces of trocar 14, electrode 16 or insulation sleeve 18. Preferably sensors 24 are positioned at trocar distal portion 14', electrode distal portion 16' and insulation sleeve distal portion 18'. Sensors 24 permit accurate measurement of temperature at a tissue site in order to determine, (i) the extent of ablation, (ii) the amount of ablation, (iii) whether or not further ablation is needed and (iv) the boundary or periphery of the ablated mass. Further, sensors 24 prevent non-targeted tissue from being destroyed or ablated.

Sensors 24 are of conventional design, including but not limited to thermistors, thermocouples, resistive wires, and the like. Suitable thermal sensors 24 include a T type thermocouple with copper constantene, J type, E type, K type, fiber optics, resistive wires, thermocouple IR detectors, and the like. It will be appreciated that sensors 24 need not be thermal sensors.

Sensors 24 measure temperature and/or impedance to permit monitoring and a desired level of ablation to be achieved without destroying too much tissue. This reduces damage to tissue surrounding the targeted mass to be ablated. By monitoring the temperature at various points within the interior of the selected tissue mass, a determination of the selected tissue mass periphery can be made, as well as a determination of when ablation is complete. If at any time sensor 24 determines that a desired ablation temperature is exceeded, then an appropriate feedback signal is received at electromagnetic energy source 20 which then regulates the amount of electromagnetic energy delivered to electrodes 16.

Thus the geometry of the ablated mass is selectable and controllable. Any number of different ablation geometries can be achieved. Creation of different ablation geometries is dependent on the length of electromagnetic energy ablation delivery surfaces, the number of electrodes, the size of the electromagnetic delivery surfaces, the amount of power delivered to the electrodes, and the duration of time for power delivery to the electrodes.

Electrode distal portions 16' can be laterally deployed relative to a longitudinal axis of trocar 14 out of an aperture 26 formed in trocar 14. Aperture 26 is at distal portion 14' or formed in a side of an exterior of electrode 14.

In one embodiment, a method for creating a volumetric ablation in a selected tissue mass provides multiple electrode ablation apparatus 10 including trocar 14 with a trocar lumen, a plurality of electrodes 16 deployable from the lumen, and an electromagnetic energy source 20 coupled to the plurality of electrodes. Trocar 14 is inserted into the selected tissue mass with the plurality of electrodes positioned in the trocar 14 lumen. The plurality of electrodes 16 are advanced from the trocar lumen in a lateral direction relative to a longitudinal axis of trocar 14 into the selected tissue mass. 10 to 50 watts, preferably 10 to 30, and still more preferably 15 to 20 watts of electromagnetic energy is delivered from electromagnetic energy source 20 to the plurality of electrodes 16 without impeding out an electrode of the plurality of electrodes. The volumetric ablation is created between the plurality of electrodes 16.

There is wide variation in the amount of deflection of electrode 16. For example, electrode 16 can be deflected a few degrees from the longitudinal axis of trocar 14, or electrodes 16 can be deflected in any number of geometric configurations, including but not limited to a "J" hook. Further, electrodes 16 are capable of being introduced from trocar 14 a few millimeters from trocar 14, or a much larger distance.

Referring now to FIG 1(b) a fluid delivery member 23 is positioned on at least a portion of an exterior of one or more of electrodes 16. Fluid delivery members are configured to be coupled to a fluid medium source 25, including but not limited to a conductive medium such as saline.

A sleeve 27 may be positioned around an exterior of fluid delivery member 23. Sleeve 27 provides for easier introduction and retraction of fluid delivery member 23 into and out of the selected tissue site. Sleeve 27 is coupled to an advancement and retraction member which may be incorporated into handpiece 12, attached to handpiece 12 or coupled to handpiece 12.

Fluid delivery member 23 is made of a material that is sufficiently porous to permit the passage of fluid conductive fluid, and in embodiment is from 0.01 to 2.0 cm thick. Fluid delivery member 23 can be made of a foam type material. Suitable materials include but are not limited to, knitted polyester, continuous filament polyester, polyester-cellulose, rayon, polyimide, polyurethane, polyethylene, and the like. Suitable commercial foams include, (i) Opcell, available from Sentinel Products Corp., Hyannis, Mass. and (ii) HT 4201 or HT 4644MD from Wilshire Contamination Control, Carlsbad, Calif. Fluid delivery member 23 has characteristics that make it particularly moldable and formable to irregular surfaces. In one embodiment, fluid delivery member 23 is made of a an open cell foam, or alternatively it can be a thermoplastic film such as polyurethane, low density polyethylene, or may be a silicone rubber. Additionally, fluid delivery member 23 can be capable of extruding conductive materials from fluid delivery member 23 itself Fluid delivery member 23 can be implanted with conductive ions, and conductive surface 32 can be coated with a material that improves its conductivity. The combination of fluid delivery member 23 and the application of the conductive solution through fluid delivery member 23 provides for an effective delivery of energy to the selected tissue site.

Another embodiment of fluid delivery member 23 is illustrated in FIG. 1(c). An expandable member 29 is at least partially positioned in an interior of introducer 14 and may be coupled to and in a surrounding relationship to an advanceable electrode 16 or to a second introducer 14". After introducer 14 has been percutaneously introduced to a selected tissue mass, expandable member 29 is introduced into the selected tissue site, such as a tumor, with the advanceable electrode 16, second introducer 14" or by itself as it is advanced out of trocar distal portion 14'. Fluid delivery member 23 is in an at least partial surrounding relationship to expandable member 29. Expandable member 29 becomes expanded with the introduction of an expansion medium, including but not limited to gas, liquid and the like, coupled to a expansion medium conduit 31. In one embodiment, the expansion medium is the conductive medium.

As expandable member 29 becomes expanded, it applies sufficient pressure to the selected tissue site which causes the site to become compressed. The compressed tissue site has less blood flow which reduces the dissipation of energy that is applied to the selected tissue site. One or more electrodes 17 is positioned at, (i) an exterior surface of expandable member 29, (ii) on an exterior surface of fluid delivery member 23, (iii) in an interior of fluid delivery member 23 or (iv) between the exterior of expandable member 29 and the exterior of fluid delivery member 23. Fluid delivery member 23 is coupled to a source of conductive medium. In one embodiment, a conductive medium conduit 33 is coupled to the source of conductive medium and fluid delivery member 23. In another embodiment, expandable member is expanded by the conductive solution and fluid delivery member receives the conductive medium from expandable member 29 which is formed of a material with a plurality of fluid apertures. Expandable member 29 may be a balloon.

As expandable member 29 becomes expanded, fluid delivery member receives energy from electrodes 17 and with helps to produce a much larger electrode when the conductive medium is introduced.

Figure 2:
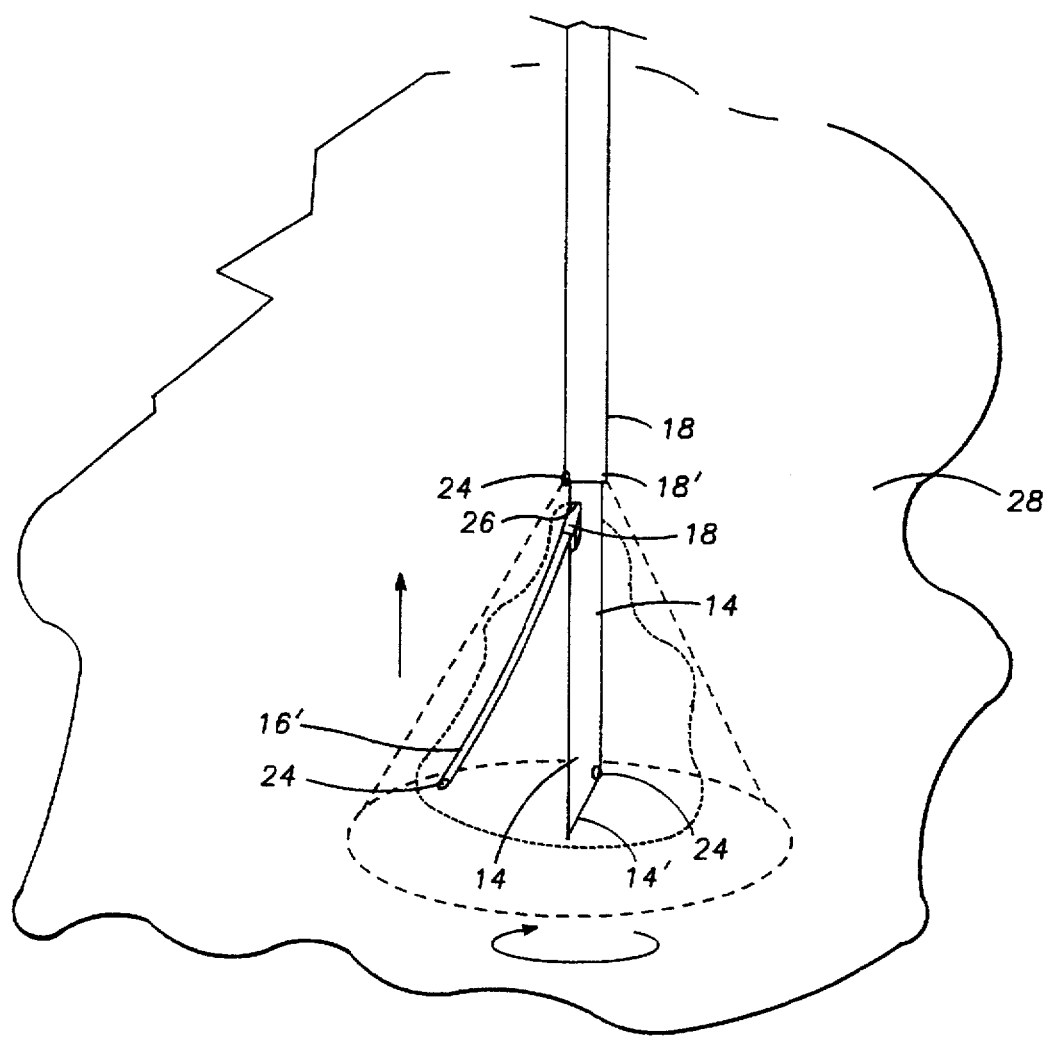
FIG. 2 is a perspective view of a conic geometric ablation achieved with the apparatus of FIG. 1(a).

As illustrated in FIG. 2, trocar 14 is introduced into a selected tissue mass 28. Three or more electrodes 17 are positioned within a trocar lumen as trocar 14 is introduced into and through the selected tissue mass. In various embodiments, 3, 4, 5, or 6 electrodes 16 are introduced laterally through trocar 14. Subsequently, electrode distal portion 16' is advanced out of aperture 26 into selected tissue mass 28. Insulation sleeves 18 are adjusted for electrodes 16. RF, microwave, short wave and the like energy is delivery to electrode 16 in a monopolar mode (RF), or alternatively, multiple electrode device 10 can be operated in a bipolar mode (RF). Multiple electrode device 10 can be switched between monopolar and bipolar operation and may have multiplexing capability between different electrodes 16. Electrode distal portions 16' is retracted back into trocar 14, and trocar is then rotated. Electrode distal portion 16' is then introduced into selected tissue mass 28. Electrodes 16 may be introduced a short distance into selected tissue mass 28 to ablate a small area, e.g., 3 cm or less. It can then be advanced further into any number of times to create more ablation zones. Again, electrode distal portion 16' is retracted back into trocar 14, and trocar 14 can be, (i) rotated again, (ii) moved along a longitudinal axis of selected tissue mass 28 to begin another series of ablations with electrode distal portions 16' being introduced and retracted in and out of trocar 14, or (iii) removed from selected tissue mass 28. A number of parameters permit ablation of selected tissue masses 28 of different sign and shapes including a series of ablations having electrodes 16 with variable length electromagnetic energy delivery surfaces and the use of one or more sensors 24.

Figure 3:
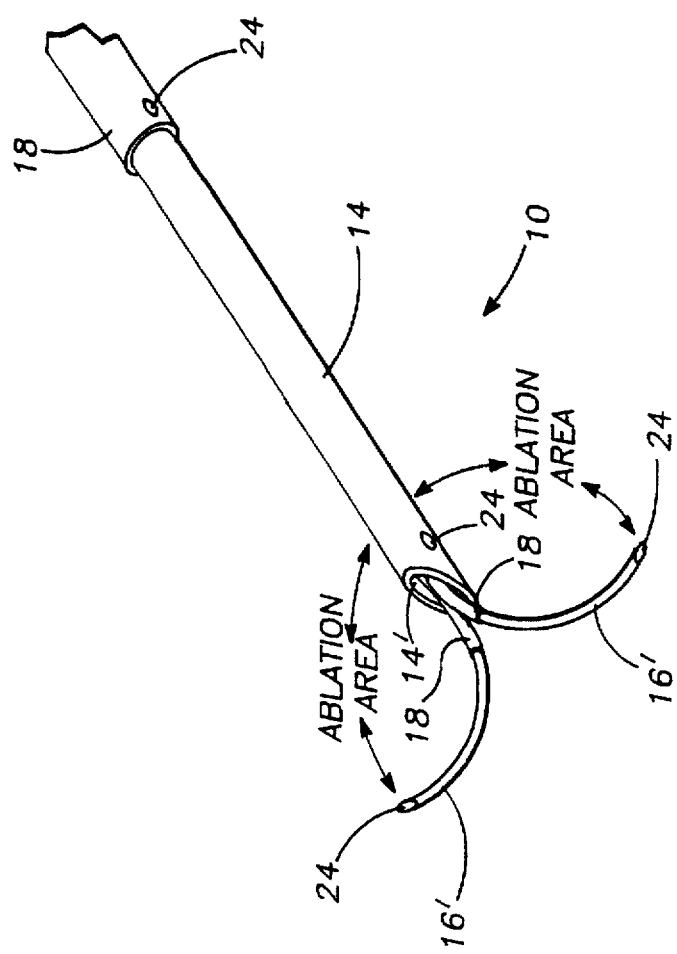
FIG. 3 is a perspective view of the multiple antenna ablation apparatus of the present invention with two antennas.

In FIG. 3, two electrodes 16 are each deployed out of distal portion 14' and introduced into selected tissue mass 28. Electrodes 16 form a plane and the area of ablation extends between the electromagnetic energy delivery surfaces of electrodes 16. Trocar 14 can be introduced in an adjacent relationship to selected tissue mass 28. This particular deployment is useful for small selected tissue masses 28, or where piercing selected tissue mass 28 is not desirable. Trocar 14 can be rotated, with electrodes 16 retracted in the lumen of trocar 14, and another ablation volume defined between the electrodes 16 is created. Further, trocar 14 can be withdrawn from its initial position adjacent to selected tissue mass 28, repositioned to another position adjacent to selected tissue mass 28, and electrodes 16 deployed to begin another ablation cycle. Any variety of different positionings may be utilized to create a desired ablation geometry for selected tissue mass of different geometries and sizes.

Figure 4:
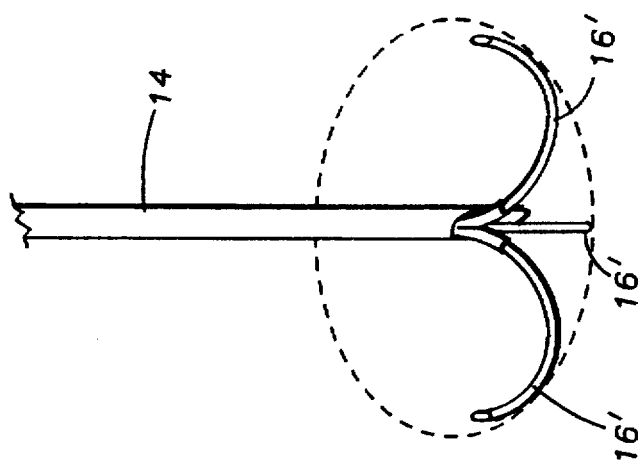
FIG. 4 is a perspective view illustrating three antennas creating a complete ablation volume.

In FIG. 4, three electrodes 16 are introduced into selected tissue mass 28. The effect is the creation of a substantially complete ablation volume formed between electrodes 16 with a minimal central core that is not ablated.

Figure 5:
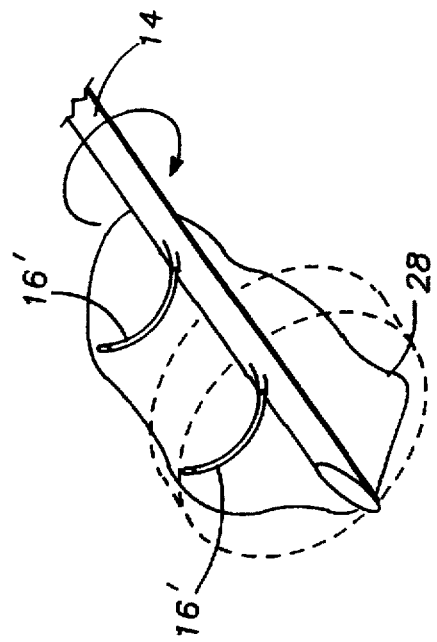
FIG. 5 is a perspective view illustrating the positioning of the multiple antenna ablation apparatus in the center of a selected tissue mass, and the creation of a cylindrical ablation.

Referring now to FIG. 5, a center of selected tissue mass 28 is pierced by trocar 14, electrodes 16 are laterally deployed and retracted, trocar 14 is rotated, electrodes 16 are deployed and retracted, and so on until a cylindrical ablation volume is achieved. Multiple electrode device 10 can be operated in the bipolar mode between the two electrodes 16, or between a electrode 16 and trocar 14. Alternatively, multiple electrode device 10 can be operated in a monopolar mode.

Electrodes 16 can serve the additional function of anchoring multiple electrode device 10 in a selected mass, as illustrated in FIGS. 6(a) and 6(b). In FIG. 6(a) one or both electrodes 16 are used to anchor and position trocar 14. Further, one or both electrodes 16 are also used to ablate tissue. In FIG. 6(b), three electrodes are deployed and anchor trocar 14.

FIG. 6(c) illustrates the infusion capability of multiple electrode device 10. Three electrodes 16 are positioned in a central lumen 14" of trocar 14. One or more of the electrodes 16 can also include a central lumen coupled to an infusion source. Central lumen 14" is coupled to an infusion source and delivers a variety of infusion mediums to selected places both within and outside of the targeted ablation mass. Suitable infusion mediums include but are not limited to, therapeutic agents, conductivity enhancement mediums, contrast agents or dyes, and the like. An example of a therapeutic agent is a chemotherapeutic agent.

Figure 8:
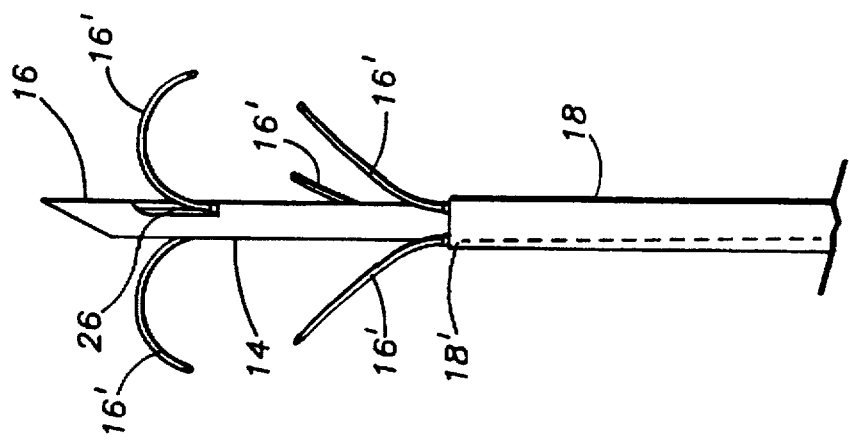
FIG. 8 is a perspective view of the multiple antenna ablation of the present illustrating the deployment of two secondary antennas from the primary antenna, and the deployment of three secondary antennas from the distal end of the insulation sleeve surrounding the primary antenna.
Figure 7:
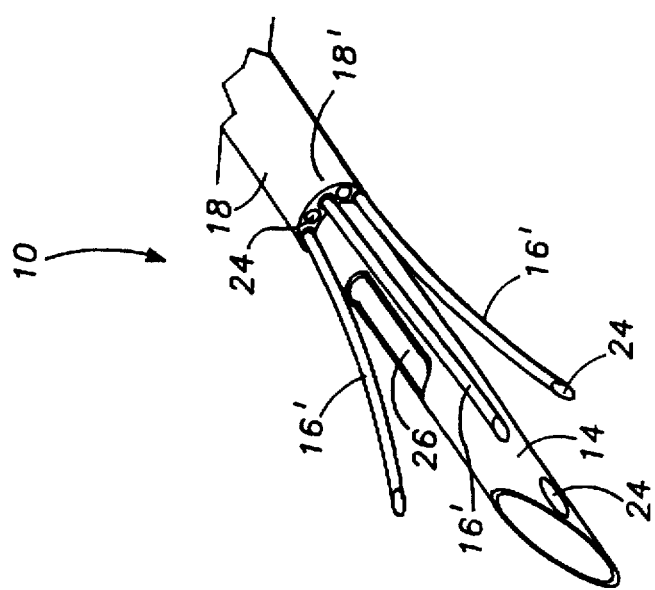
FIG. 7 is a perspective view of the multiple antenna ablation of the present invention illustrating the deployment of three secondary antennas from a distal end of the insulation sleeve surrounding the primary antenna.

As shown in FIG. 7, insulation sleeve 18 can include one or more lumens for receiving electrodes 16 which are deployed out of an insulation sleeve distal portion 18'. FIG. 8 illustrates two electrodes 16 being introduced out of insulation sleeve distal portion 18', and two electrodes 16 introduced through apertures 26 formed in trocar 14. As illustrated, electrodes 16 introduced through apertures 26 provide an anchoring function. FIG. 8 illustrates that electrodes 16 can have a variety of different geometric configurations in multiple electrode device 10.

A feedback control system 29 is connected to electromagnetic energy source 20, sensors 24 and electrodes 16. Feedback control system 29 receives temperature or impedance data from sensors 24 and the amount of electromagnetic energy received by electrodes 16 is modified from an initial setting of ablation energy output, ablation time, temperature, and current density (the "Four Parameters"). Feedback control system 29 can automatically change any of the Four Parameters. Feedback control system 29 can detect impedance or temperature and change any of the Four Parameters. Feedback control system 29 can include a multiplexer to multiplex different electrodes, a temperature detection circuit that provides a control signal representative of temperature or impedance detected at one or more sensors 24. A microprocessor can be connected to the temperature control circuit.

The following discussion pertains particularly to the use of an RF energy source and RF electrodes. It will be appreciated that devices similar to those associated with RF multiple electrode device 10 can be utilized with laser optical fibers, microwave devices and the like.

Referring now to FIG. 9, all or portions of feedback control system 29 are illustrated. Current delivered through electrodes 16 is measured by current sensor 30. Voltage is measured by voltage sensor 32. Impedance and power are then calculated at power and impedance calculation device 34. These values can then be displayed at user interface and display 36. Signals representative of power and impedance values are received by controller 38.

A control signal is generated by controller 38 that is proportional to the difference between an actual measured value, and a desired value. The control signal is used by power circuits 40 to adjust the power output in an appropriate amount in order to maintain the desired power delivered at electrodes 16.

In a similar manner, temperatures detected at sensors 24 provide feedback for determining the extent of ablation, and when a completed ablation has reached the physical location of sensors 24. The actual temperatures are measured at temperature measurement device 42 and the temperatures are displayed at user interface and display 36. A control signal is generated by controller 38 that is proportional to the difference between an actual measured temperature, and a desired temperature. The control signal is used by power circuits 40 to adjust the power output in an appropriate amount in order to maintain the desired temperature delivered at the respective sensor 24. A multiplexer can be included to measure current, voltage and temperature, at the numerous sensors 24, and energy is delivered to electrodes 16.

Controller 3 8 can be a digital or analog controller, or a computer with software. When controller 38 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface and display 36 includes operator controls and a display. Controller 3 8 can be coupled to imaging systems, including but not limited to ultrasound, CT scanners, X-ray, MRI, mammographic X-ray and the like. Further, direct visualization and tactile imaging can be utilized.

The output of current sensor 30 and voltage sensor 32 is used by controller 3 8 to maintain a selected power level at electrodes 16. The amount of RF energy delivered controls the amount of power. A profile of power delivered can be incorporated in controller 38, and a preset amount of energy to be delivered can also be profiled.

Circuitry, software and feedback to controller 38 result in process control, and the maintenance of the selected power, and are used to change, (i) the selected power, including RF, microwave, laser and the like, (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 24.

Figure 10:
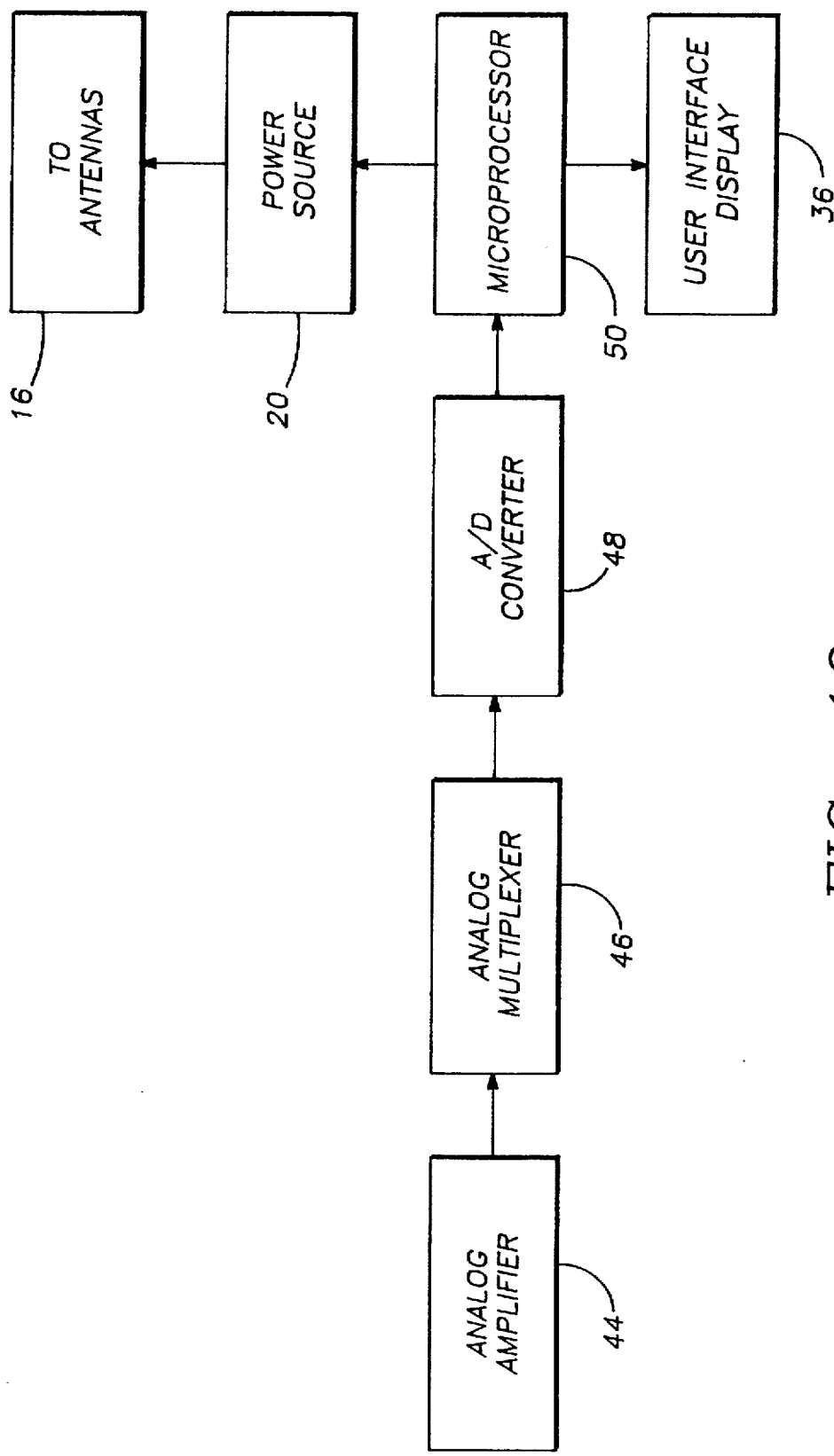
FIG. 10 is a block diagram illustrating an analog amplifier, analog multiplexer and microprocessor used with the present invention.

Referring now to FIG. 10, current sensor 30 and voltage sensor 32 are connected to the input of an analog amplifier 44. Analog amplifier 44 can be a conventional differential amplifier circuit for use with sensors 24. The output of analog amplifier 44 is sequentially connected by an analog multiplexer 46 to the input of A/D converter 48. The output of analog amplifier 44 is a voltage which represents the respective sensed temperatures. Digitized amplifier output voltages are supplied by A/D converter 48 to a microprocessor 50. Microprocessor 50 may be Model No. 68HCII available from Motorola. However, it will be appreciated that any suitable microprocessor or general purpose digital or analog computer can be used to calculate impedance or temperature.

Microprocessor 50 sequentially receives and stores digital representations of impedance and temperature. Each digital value received by microprocessor 50 corresponds to different temperatures and impedances.

Calculated power and impedance values can be indicated on user interface and display 36. Alternatively, or in addition to the numerical indication of power or impedance, calculated impedance and power values can be compared by microprocessor 50 with power and impedance limits. When the values exceed predetermined power or impedance values, a warning can be given on user interface and display 36, and additionally, the delivery of RF energy can be reduced, modified or interrupted. A control signal from microprocessor 50 can modify the power level supplied by electromagnetic energy source 20.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An ablation apparatus, comprising:
    an introducer including an introducer lumen, a proximal portion and a distal portion;
    a handpiece with a proximal portion and a distal portion coupled to the introducer proximal portion;
    two or more electrodes at least partially positioned in the introducer lumen, wherein each electrode is configured to be advanced from the introducer distal portion in a deployed state into a selected tissue site to define a volumetric ablation volume;
    a porous fluid delivery member positioned on at least a portion of an exterior of one of the electrodes, wherein the fluid delivery member is configured to be coupled to a fluid medium source; and
    a cable coupled to the electrodes.

2. The apparatus of claim 1, wherein a distal portion of the introducer is an electrode.

3. The apparatus of claim 1, wherein the electrodes are RF electrodes.

4. The apparatus of claim 1, further comprising:

a sheath at least partially positioned around the fluid delivery member.

5. The apparatus of claim 4, wherein the sheath is slideable along an exterior of the fluid delivery member.

6. The apparatus of claim 1, wherein each electrode has at least one radius of curvature when advanced from introducer distal portion.

7. The apparatus of claim 1, further comprising:

an electrode advancement and retraction device coupled to the electrodes to advance and retract the electrodes in and out of the distal portion of the introducer.

8. The apparatus of claim 7, further comprising:

an insulation sleeve positioned around at least a portion of the introducer.

9. The apparatus of claim 1, further comprising:

an insulation sleeve positioned around at least a portion of an exterior surface of an electrode.

10. The apparatus of claim 1, wherein the fluid delivery member is at least partially made of an open cell foam.

11. The apparatus of claim 1, wherein the fluid delivery member includes a lumen coupled to an electrolytic solution source.

12. The apparatus of claim 11, wherein the electrolytic solution is saline.

* * * * *